(12) United States Patent
Lee et al.

(10) Patent No.: US 6,204,047 B1
(45) Date of Patent: Mar. 20, 2001

(54) GROWTH DIFFERENTIATION FACTOR-10

(75) Inventors: Se-Jin Lee, Baltimore; Noreen Cunningham, deceased, late of Silver Spring, both of MD (US), by John Cunningham, executor

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 08/624,635

(22) PCT Filed: Oct. 7, 1994

(86) PCT No.: PCT/US94/11440

§ 371 Date: Oct. 10, 1996

§ 102(e) Date: Oct. 10, 1996

(87) PCT Pub. No.: WO95/10539

PCT Pub. Date: Apr. 20, 1995

Related U.S. Application Data

(63) Continuation-in-part of application No. 08/134,078, filed on Oct. 8, 1993, now abandoned.

(51) Int. Cl.[7] .......................... C12N 15/12; C07K 14/51
(52) U.S. Cl. .................................. 435/252.3; 435/320.1; 530/399; 536/23.5
(58) Field of Search .......... 530/395; 435/252.3, 435/320.1; 536/23.5

(56) References Cited

U.S. PATENT DOCUMENTS 5,468,845 * 11/1995 Oppermann et al. .............. 530/387.9

FOREIGN PATENT DOCUMENTS

WO 94/01557  1/1994  (WO).

OTHER PUBLICATIONS

Wozney et al. Science 242, 1528–1534, 1988.*

S. Lee, Expression of growth/differentiation factor 1 in the nervous system: Conservation of a bicistronic structure, *Proceedings of the National Academy of Sciences USA*, vol. 88, May 1991, pp. 4250–4254.

Alexandra C. McPherron et al., GDF–3 and GDF–9: Two New Members of the Transforming Growth Factor–β Superfamily Containing a Novel Pattern of Cysteines*, *Journal of Biological Chemistry*, vol. 268, No. 5, Feb. 15, 1993, pp. 3444–3449.

C. Michael Jones et al., Isolation of Vgr–2, a Novel Member of the Transforming Growth Factor–β–Related Gene Family, *Molecular Endocrinology*, vol. 6, No. 11, 1992, pp. 1961–1968.

S. Lee, Identification of a Novel Member (GDF–1) of the Transforming Growth Factor–β Superfamily, *Molecular Endocrinology*, vol. 4, No. 7, 1990, pp. 1034–1039.

* cited by examiner

*Primary Examiner*—Stephen Walsh
*Assistant Examiner*—Karen E. Brown
(74) *Attorney, Agent, or Firm*—Gray Cary Ware & Freidenrich LLP; Lisa A. Haile

(57) ABSTRACT

Growth differentiation factor-10 (GDF-10) polypeptide is disclosed as well as polynucleotides encoding GDF-10, vectors and host cells.

11 Claims, 6 Drawing Sheets

```
   1  TGGGGTCATCCGGGCTGTGTCCGAGTCCCACAGGAGACAACTCCAGCCCGCGGACGAGGTGCAC      60
  61  AGCCAACACTGGCTGAGCCCCTCCAGTCCTGTCTGTTCTCCTGGCTCCTCAGACCCTTCACCACCGTTACT   120
 121  CAGCCATGGCTCCAGGTCCTGCTCCTGCTCCGGATCAGTCTGGGTCCCAGTGCTGCCATGGTGC    180
                M   A   P   G   P   A   R   I   S   L   G   S   Q   L   L   P   M   V   P
 181  CGCTGCTCCTGCTGCTGCGGGGCGCAGGCTGCGGCCACAGGGGCCCCTCATGTGTCCTCAT       240
             L   L   L   L   R   G   A   G   C   G   H   R   G   P   S   W   S   S   L
 241  TGCCCCTGGCAGTCGCCGGTCTGCAGGGGACTCCGCAGCAGTCACCCGGGGACG              300
             P   S   A   A   G   L   Q   G   D   R   D   S   Q   Q   S   P   G   D   A
 301  CAGCAGCCGCTCTGGGCCCCAGGCGCCCAGGACATGTCGCTATCCACATGCTCAGGCTCT         360
             A   A   L   G   P   G   A   Q   D   M   V   A   I   H   M   L   R   L   Y
 361  ATGAGAAGTACAACCGAAGAGGTGCTCCACCGGAGGAGCAACACCGTCCGAAGCTTCC          420
             E   K   Y   N   R   R   G   A   P   P   G   G   N   T   V   R   S   F   R
 421  GTGCCCGGCTGGAAATGATCGACACAGCCGCTGTGTATTTCTTCAACTTGACTTCCATGC        480
             A   R   L   E   M   I   D   Q   K   P   V   Y   F   F   N   L   T   S   M   Q
 481  AAGACTCAGAATCCTCACAGCCGCCTTCCACTTCAGAACCTCCACGGTGGC                 540
             D   S   E   M   I   L   T   A   A   F   H   F   Y   S   E   P   P   R   W   P
 541  CCCGGGCTGGTGAGGTATTCTGCAAGCCCGAGTCTAAGAACGCATCCTGCCGCTCCTGA         600
             R   A   G   E   V   F   C   K   P   R   A   K   N   A   S   C   R   L   L   T
 601  CCCCAGGGCTGCCTGCACGCTTGCACTTAATCTTCCGCAGTCTTTCCAGAACACCGCCA         660
             P   G   L   P   A   R   L   H   L   I   F   R   S   L   S   Q   N   T   A   T
 661  CTCAGGGGCTGCTCCGGGGCGCCATGGCTCAAGGCTGCCCGAAGGGATGGAGAGCCTGTGGCAGG    720
             Q   G   L   L   R   G   A   M   A   L   T   P   P   P   R   G   L   W   Q   A
 721  CCAAGGACATCTCCTCAATCATCAAGGCTCGGCGGGACGGCGAGCTGCTCCTCTCTGCCCT       780
             K   D   I   S   I   I   K   A   R   R   D   G   E   L   L   L   S   A
 781  CTCAGCTGGATACTGGGGAGAAGGACCCCGGAGTCCCGAACCTCCGAACCATGCCCT           840
             Q   L   D   T   G   E   K   D   P   G   V   P   R   P   S   S   H   M   P   Y
 841  ATATCCTTGTCTACGCCAATGACCTGGCCATCTCCGAACCCAACAGTGTAGCAGTGTCGC        900
             I   L   V   Y   A   N   D   L   A   I   S   E   P   N   S   V   A   V   S   L
 901  TACAGAGATACGACCCCATTTCCAGCTGGAGACTTTGAGCCTGGAGCAGCCCCAACAGCT        960
             Q   R   Y   D   P   P   P   A   G   D   F   E   P   G   A   A   P   N   S   S
 961  CAGCTGATCCCCCGCGTGCGCAGGCGGCGGCCAGGGCTCAAAACCCCTGCAAGACAATGAAC   1020
             A   D   P   R   V   R   R   A   A   Q   V   S   K   P   L   Q   D   N   E   L
```

FIG. 2A

```
1021  TGCCGGGGCTGGATGAAAGACCAGCGCCTGCCCTGCCATGCCCAGAATTTCCACAAGCACG  1080
         P  G  L  D  E  R  P  A  P  A  L  H  A  Q  N  F  H  K  H  E
1081  AGTTCTGGTCCAGTCCTTTCGGGCACTGAAACCCCGCACGGGCGCAAAGACCGCAAGA    1140
         F  W  S  S  P  F  R  A  L  K  P  R  T  A  R  K  D  R  K  K
1141  AGAAGGACCAGGACACATTCACCGCCGCCTCCTCTCAGGTGCTGGACTTTGACGAGAAGA  1200
         K  D  Q  D  T  F  T  A  A  S  S  Q  V  L  D  F  D  E  K  T
1201  CGATGCAGAAAGCCAGGAGGCGGCAGGGATGAGCCCGGGTCTGCTCCAGGAGGTACC     1260
         M  Q  K  A  R  R  R  Q  W  D  E  P  R  V  C  S  R  R  Y  L
1261  TGAAGGTGGATTTTGCAGACATCGGGTGCTGGAATGAATGGGAGATCATCTCTCCAAATCCTTTG  1320
         K  V  D  F  A  D  I  G  W  N  E  W  I  I  S  P  K  S  F  D
1321  ACGCCTACTACTGTGCTGGGGCCTGCGAGTTCCCCATGCCCAAGATTGTCCGCCCATCCA  1380
         A  Y  Y  C  A  G  A  C  E  F  P  M  P  K  I  V  R  P  S  N
1381  ACCATGCCACCATCCAGAGCATCGTCAGAGCTGTGGGCATTGTCCCTGGCATCCCAGAGC  1440
         H  A  T  I  Q  S  I  V  R  A  V  G  I  V  P  G  I  P  E  P
1441  CATGCTGTGTTCCAGACAAGATGAACTCCCTTGGAGTCCTTTTCCTGGATGAAAATCGGA  1500
         C  C  V  P  D  K  M  N  S  L  G  V  L  F  L  D  E  N  R  N
1501  ATGCGGGTTCTGAAGGTGTACCCCAATATGTCCGTAGAGACCTGTGCTGTCGGTAAGATG  1560
         A  V  L  K  V  Y  P  [N  M  S]  V  E  T  C  A  C  R  *
1561  GCTTCAAGATACAGAAGACACAGACCTGCTTCATCCCTGCCCCTGCCCAGAGTGGACAATCTTGGAGC  1620
1621  CAGGGACTTGACTCGGGGAGGTTCCAGGTTCCAGGTGCTCCAGGTTACAGGCAGCCCTGCTGG  1680
1681  GACCAAGAAAGATCTGCCCACCACAGATCTTCCAGTTCTTCAGTTCTTCCGTGCTGGTAGC  1740
1741  TCTGTAAAGACCTGTTGAGTTCTGAGTCCTGGAAGAATCTGGAATTAACTGTGGTCTGCAATTTG  1800
1801  CCCATCATCCCTGCCCACACTTTTCAAGGCCTAGAAGGCCTAGAAATAACGTGTGTCCTCAAATGTCAA  1860
1861  CTCCAGGCATTGTCCTCTCAAAACCTAGAAGACTATGCAAATCTTGGGGTACTCCCCC  1920
1921  CCCCATGGCAGTTGTTTAAAATGCTGTTTTAAACCCTGCCATTCTAGAAACAGGGCC    1980
1981  TAACCCATGGCACGAGTGATATTTCTCTTACGTTTCACTACACGTGCTTTATACATG    2040
2041  CAGTATGCACATGTAATCACGGTTGATTCTTCTTCTTTAATATATGTATTTCTATTTCAAA  2100
2101  GCAAAACGGAGAGAGTCGATCCCATCCCTGCAGAGGTAATAATGCTGGAATAATGCAAGTTAGGTGTGGG  2160
2161  TTGTCTAAGCATGTGTATGGAAATAATACATACTTTGTAATTATACTGTTGAATACTAAAAAAGT  2220
2221  AACCAAGATTTTATATTTTTGTAAATAAAATTAAAGGTTGTATAACTGTGAGTGTTCTG    2280
2281  TGTTTTTATGGAAAGCTAATAAATTAAAGGTGCCGAGGTATC  2322
```

FIG. 2B

```
GDF-10      EKSMQKARRRQWDEPRVC SRRYLKVDF-ADIGWNEWIISPKSFDAYYC AGAC EFPMPKIVRPS---
GDF-1       RPRRDAEPVLGGPGGA    RARRLYVSF-REVGWHRWVIAPRGFLANYC QGAC ALPVALSGSGGPP
GDF-3       RKRRAAISVPKGFCRNFC   HRHQLFINF-QDLGWHKWVIAPKGFMANYC HGEC PFSMTTYLNS---
GDF-9       SFNLSEYFKQFLFPQNEC   ELHDFRLSF-SQLKWDNWIVAPHRYNPRYC KGDC PRAVRHRYGS---
BMP-2       REKRQAKHKQRKRLKSSC    KRHPLYVDF-SDVGWNDWIVAPPGYHAFYC HGEC PFPLADHLNS---
BMP-4       KRSPKHHSQRARKKNKNC    RRHSLYVDF-SDVGWNDWIVAPPGYQAFYC HGDC PFPLADHLNS---
Vgr-1       SRGSGSSDYNGSELKTAC    KKHELYVSF-QDLGWQDWIIAPKGYAANYC DGEC SFPLNAHMNA---
OP-1        LRMANVAENSSSDQRQAC    KKHELYVSF-RDLGWQDWIIAPEGYAAYYC EGEC AFPLNSYMNA---
BMP-5       SRMSSVGDYNTSEQKQAC    KKHELYVSF-RDLGWQDWIIAPEGYAAFYC DGEC SFPLNAHMNA---
OP-2        RLPGIFDDVHGSHGRQVC    RRHELYVSF-QDLGWLDWVIAPQGYSAYYC EGEC SFPLDSCMNA---
BMP-3       EQTLKKARRKQWIEPRNC    ARRYLKVDF-ADIGWSEWIISPKSFDAYYC SGAC QFPMPKSLKPS---
MIS         GPGRAQRSAGATAADGPC    ALRELSVDL---RAERSVLIPETYQANNC QGVC GWPQSDRNPRY---
Inhibin α   ALRLLQRPPEEPAAHANC    HRVALNISF-QELGWERWIVYPPSFIFHYC HGGC GLHIPPNLSLPV
Inhibin βA  RRRRGLECDGKV--NIC     KKQFFVSF-KDIGWNDWIIAPSGYHANYC EGEC PSHIAGTSGSSL
Inhibin βB  RIRKRGLECDGRT--NLC    CRQQFFIDF-RLIGWNDWIIAPTGYYGNYC EGSC PAYLAGVPGSAS-
Nodal       GWGRRQRRHHLPDRSQLC    RRVKFQVDF-NLIGWGSWIIYPKQYNAYRC EGEC PNPVGEEFHP---
TGF-β1      RRALDTNYCFSSTE-KNC    CVRQLYIDFRKDLGWKWIHEPKGYHANFC LGPC PYIWSLD-----
TGF-β2      KRALDAAYCFRNVQ-DNC    CLRPLYIDFKRDLGWKWIHEPKGYNANFC AGAC PYLWSSD-----
TGF-β3      KRALDTNYCFRNLE-ENC    CVRPLYIDFRQDLGWKWVHEPKGYYANFC SGPC PYLRSAD-----
```

FIG. 3A

```
GDF-10     --NHATIQSIVRA-VGIVPGIPEPCCV---PDKMNSLGVLFL-DENRNAVLKVYPNMSVETCACR
GDF-1      ALNHAVLRALMHA--AAPGAADLPCCV---PARLSPISVLFF-DNSDNVVLRQYEDMVVDECGCR
GDF-3      -SNYAFMQALMHM---ADPKVPKAVCV---PTKLSPISMLYQ-DSDKNVILRHYEDMVVDECGCG
GDF-9      -PVHTMVQNIIYE--KLDPSVPRPSCV---PGKYSPLSVLTI-EPDGSIAYKEYEDMIATRCTCR
BMP-2      -TNHAIVQTLVNS---VNSKIPKACCV---PTELSAISMLYL-DENEKVVLKNYQDMVVEGCGCR
BMP-4      -TNHAIVQTLVNS---VNSSIPKACCV---PTELSAISMLYL-DEYDKVVLKNYQEMVVEGCGCR
Vgr-1      -TNHAIVQTLVHL--MNPEYVPKPCCA---PTKLNAISVLYF-DDNSNVILKKYRNMVVRACGCH
OP-1       -TNHAIVQTLVHF---INPETVPKPCCA---PTQLNAISVLYF-DDSSNVILKKYRNMVVRACGCH
BMP-5      -TNHAIVQTLVHL--MFPDHVPKPCCA---PTKLNAISVLYF-DDSSNVILKKYRNMVVRSCGCH
OP-2       -TNHAILQSLVHL--MKPNAVPKACCA---PTKLSATSVLYY-DSSNNVILRKARNMVVKACGCH
BMP-3      -NHATIQSIVRA-VGVVPGIPEPCCV---PEKMSSLSILFF-DENKNVLKVYPNMTVESCACR
MIS        -GNHVVLLKMQA--RGAALARPCCV---PTAYAGKLLISLSEER--ISAHHVPNMVATECGCR
Inhibin α   -PGAPPTPAQPYS---LLPGAQPCCAALPGTMRPLHVRTTSDGGYSFKYETVPNLLTQHCACI
Inhibin βA  -SFHSTVINHYRMRGHSPFANLKSCCV---PTKLRPMSMLYY-DDGQNIIKKDIQNMIVEECGCS
Inhibin βB  -SFHTAVVNQYRMRGLNPGT-VNSCCI---PTKLSTMSMLYF-DDEYNIVKRDVPNMIVEECGCA
Nodal      -TNHAYIQSLLKR--YQPHRVPSTCCA---PVKTKPLSMLYV-DNGRVLLEHHKDMIVEECGCL
TGF-β1     -TQYSKVLALYNQ--HNPGASAAPCCV---PQALEPLPIVYY-VGRKPKV-EQLSNMIVRSCKCS
TGF-β2     -TQHSRVLSLYNT---INPEASASPCCV---SQDLEPLTILYY-IGKTPKI-EQLSNMIVKSCKCS
TGF-β3     -TTHSTVLGLYNT---LNPEASASPCCV---PQDLEPLTILYY-VGRTPKV-EQLSNMVVKSCKCS
```

FIG. 3B

|  | % amino acid identity with GDF-10 |
|---|---|
| GDF-1 | 38% |
| GDF-3 | 37% |
| GDF-9 | 28% |
| BMP-2 | 46% |
| BMP-4 | 45% |
| Vgr-1 | 43% |
| OP-1 | 41% |
| BMP-5 | 41% |
| OP-2 | 39% |
| BMP-3 | 83% |
| MIS | 31% |
| Inhibin α | 28% |
| Inhibin βA | 36% |
| Inhibin βB | 35% |
| Nodal | 40% |
| TGF-β1 | 30% |
| TGF-β2 | 30% |
| TGF-β3 | 29% |

FIG. 4

```
KARRKQWDEPRVCSRRYLKVDFADIGWNEWIISPKSFDAYYCAGACEFPM
||||:|||||||||||||||||||||||||||||||||||||||||||||
KARRRQWDEPRVCSRRYLKVDFADIGWNEWIISPKSFDAYYCAGACEFPM

PKIVRPSNHATIQSIVRAVGIIPGIPEPCCVPDKMNSLGVLFLDENRNVV
|||||||||||||||||||||||:||||||||||||||||||||||||.|
PKIVRPSNHATIQSIVRAVGIVPGIPEPCCVPDKMNSLGVLFLDENRNAV

LKVYPNMSVDTCACR
|||||||||:|||||
LKVYPNMSVETCACR
```

FIG. 5

GROWTH DIFFERENTIATION FACTOR-10

This application is a §371 of PCT/US94/11440 filed on Oct. 7, 1994, which is continuation-in-part of U.S. application Ser. No. 08/134,078 filed on Oct. 8, 1993 now abandoned.

BACKGROUND OF THE INVENTION

1. Field of the Invention

The invention relates generally to growth factors and specifically to a new member of the transforming growth factor beta (TGF-β) superfamily, which is denoted, growth differentiation factor-10 (GDF-10).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., *Nature,* 345:167, 1990), Drosophila decapentaplegic (DPP) gene product, which is required for dorsal-ventral axis formation and morphogenesis of the imaginal disks (Padgett, et al., *Nature,* 325: 1–84, 1987), the Xenopus Vg-1 gene product, which localizes to the vegetal pole of eggs ((Weeks, et al., *Cell,* 51:861–867, 1987), the activins (Mason, et al., *Biochem, Biophys. Res. Commun.,* 135:957–964, 1986), which can induce the formation of mesoderm and anterior structures in Xenopus embryos (Thomsen, et al., *Cell,* 63:485, 1990), and the bone morphogenetic proteins (BMPS, osteogenin, OP-1) which can induce de novo cartilage and bone formation (Sampath, et al., *J. Biol. Chem.,* 265:13198,1990). The TGF-βs can influence a variety of differentiation processes, including adipogenesis, myogenesis, chondrogenesis, hematopoiesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mat regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has bee found to be biologically active, but for other family members, like he inhibins (Ling, et al., *Nature,* 321:779, 1986) and the TGF-βs (Cheifetz, et al., *Cell,* 48:409, 1987), heterodimers have also been detected, and these appear to have different biological properties than the respective homodimers.

Identification of new factors that are tissue-specific in their expression pattern will provide a greater understanding of that tissue's development and function and allow development of effective diagnostic and therapeutic regimens.

SUMMARY OF THE INVENTION

The present invention provides a cell growth and differentiation factor, GDF-10, a polynucleotide sequence which encodes the factor, and antibodies which are immunoreactive with the factor. This factor appears to relate to various cell proliferative disorders, especially those involving those involving uterine, nerve, bore, and adipose tissue.

Thus, in one embodiment, the invention provides a method for detecting a cell proliferative disorder of uterine, nerve, or fat origin and which is associated with GDF-10. In another embodiment, the invention provides a method for treating a cell proliferative disorder by suppressing or enhancing GDF-10 activity.

BRIEF DESCRIPTION OF THE DRAWINGS

FIG. 2A and 2B show nucleotide and predicted amino acid sequence of murine GDF-10 (SEQ ID NO:4 and SEQ ID NO:5). Consensus N-glycosylation signals are denoted by plain boxes.

FIG. 3A and 3B show the alignment of the C-terminal sequences of GDF-10 (SEQ ID NO:5) with other members of the TGF-β superfamily (SEQ ID NO:7–24), respectively. The conserved cysteine residues are boxed. Dashes denote gap introduced in order to maximize alignment.

FIG. 4 shows amino acid homologies with different members of the TGF-β superfamily. Numbers represent percent amino acid identities between each pair calculated from the first conserved cysteine to the C-terminus.

FIG. 5 shows an alignment of the C-terminal sequences of human (SEQ ID NO:26) (top lines) and murine (SEQ ID NO:25) (bottom lines) GDF-10.

FIG. 6 shows an autoradiogram of labeled secreted proteins synthesized by 293 cells transfected with a pcDNAI vector into which the GDF-10 cDNA was inserted in either the antisense (lanes 1 and 2) or sense (lanes 3 and 4) orientation.

DETAILED DESCRIPTION OF THE INVENTION

Figure 1:
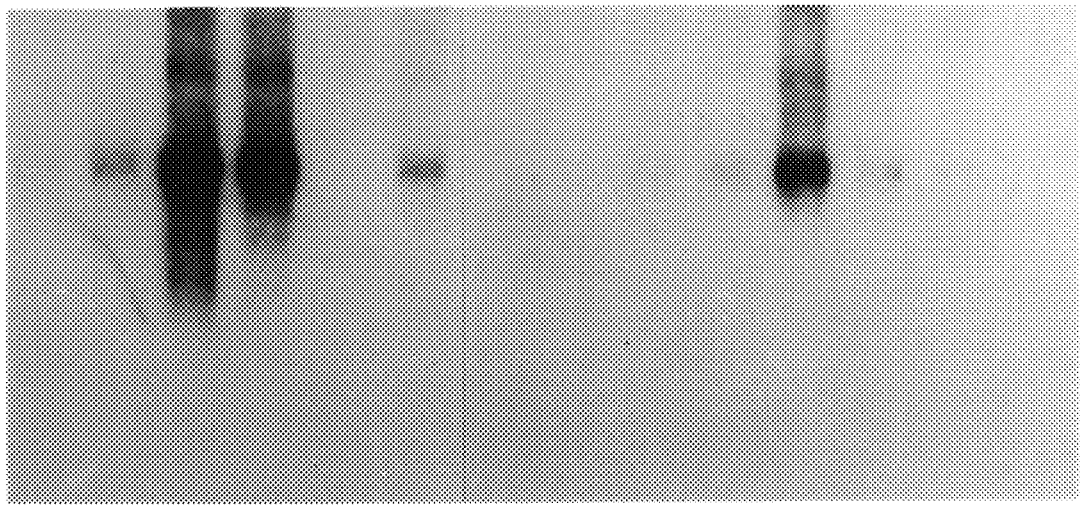
FIG. 1 shows expression of GDF-10 mRNA in adult tissues.

The present invention provides a growth and differentiation factor, GDF-10 and a polynucleotide sequence encoding GDF-10. GDF-10 is expressed at highest levels in uterus and fat and at lower levels in other tissues, such as brain. In one embodiment, the invention provides a method for detection of a cell proliferative disorder of uterine, nerve, or fat origin which is associated with GDF-10 expression. In another embodiment, the invention provides a method for treating a cell proliferative disorder by using an agent which suppresses or enhances GDF-10 activity.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-10 protein of this invention and the members of the TGF-β family, indicates that GDF-10 is a new member of the family of growth and differentiation factors. Based on the known activities of many of the other members, it can be expected that GDF-10 will also possess biological activities that will make it useful as a diagnostic and therapeutic reagent.

The expression of GDF-10 in uterine and fat issue suggests a variety of applications using the polypeptide, polynucleotide, and antibodies of the invention, related to contraception, fertility, pregnancy, and cell proliferative diseases. Abnormally low levels of the factor my be indicative of impaired function in the uterus while abnormally high levels may be indicative of hypertrophy, hyperplasia, or the presence of ectopic tissue. Hence, GDF-10 my be useful in detecting not only primary and metastatic neoplasms of uterine origin but in detecting diseases such as endometriosis as well. In addition, GDF-10 may also be useful as an indicator of developmental anomalies in prenatal screening procedures.

Several members of the TGF-β superfamily possess activities suggesting possible applications for the treatment of cell proliferative disorders, such as cancer. In particular, TGF-β has been shown to be potent growth inhibitor for a variety of cell types (Massague, Cell 49:437, 1987). MIS has been shown to in inhibit the growth of human endometrial carcinoma tumors in nude amine (Donahoe, et al., Ann. Surg. 194:472, 1981), and inhibin α has been shown to suppress the development of tumors both in the ovary an in the testis (Matzuk, et al., Nature, 360:313, 1992). GDF-10 may have similar activity and may therefore be useful as an antiproliferative agent, such as for the treatment of endometrial cancer or endometriosis.

Many of the members of the TGF-β family are also important mediators of tissue repair. TGF-β has been shown to have marked effects on the formation of collagen and causes of striking angiogenic response in the newborn mouse (Roberts, et al, Proc. Nat'l Acad. Sci., USA 83:4167, 1986). The BMP's can induce new bone growth and are effective for the treatment of fractures and other skeletal effects (Glowacki, et al., Lancet, 1:959, 1981; Ferguson, et al., Clin. Orthoped. Relat Res., 227:265, 1988; Johnson, et al., Clin Orthoped Relat. Res., 230:257, 1988). Based on the high degree of homology between GDF-10 and BMP-3, GDF-10 may have similar activities and may be useful in repair of tissue injury caused by trauma or burns for example.

GDF-10 may play a role in regulation of the menstrual cycle or regulation of uterine function during pregnancy, and therefore, GDF-10, anti-GDF-10 antibodies, or antisense polynucleotides may be useful either in contraceptive regimens, in enhancing the success of in vitro fertilization procedures, or in preventing premature labor.

Certain members of this superfamily have expression patterns or possess activities that relate to the function of the nervous system. For example, one family member, namely GDNF, has been shown to be a potent neurotrophic factor that can promote the survival of dopaminergic neurons (Lin, et al., Science, 260:1130). Another family member, namely dorsalin, is capable of promoting the differentiation of neural crest cells (Baster, et al., Cell, 73:687). The inhibins and activins have been shown to be expressed in the brain (Meunier, et al., Proc. Nat'l Acad. Sci., USA, 85:247, 1988; Sawchenko , et al., Nature, 334:615, 1988), and activin has been shown to be capable of functioning as a nerve cell survival molecule (Schubert, et al., Nature, 344:868, 1990). Another family member, namely GDF-1, is nervous system-specific in its expression pattern (Lee, Proc. Nat'l Acad. Sci., USA, 88:4250,1991), and certain other family members, such as Vgr-1 (Lyons, et al., Proc. Nat'l Acad. Sci., USA, 86:4554, 1989; Jones et al., Development, 111:581, 1991), OP-1 (Ozkaynak, et al., J. Biol. Chem., 267:25220, 1992), and BMP-4 (Jones, et al., Development 111:531, 1991), are also known to be expressed in the nervous system. By analogy GDF-10 may have applications in the treatment of neurodegenerative diseases or in maintaining cells or tissues in culture prior to transplantation.

The expression of GDF-10 in adipose tissue also raises the possibility of applications for GDF-10 in the treatment of obesity or of disorders related to abnormal proliferation of adipocyte. In this regard, TGF-β has been shown to be a potent inhibitor of adipocyte differentiation in vitro (Ignotz and Massague, Proc. Natl. Acad. Sci., USA 82:8530, 1985).

The term "substantially pure" as used herein refers to GDF-10 which is substantially free of other proteins, lipids carbohydrates or other materials with which it is naturally associated. One skilled in the art can purify GDF-10 using standard techniques for protein purification. The substantially pure polypeptide will yield a single major band on a non-reducing polyacrylamide gel. The purity of the GDF-10 polypeptide can also be determined by amino-terminal amino acid sequence analysis. GDF-10 polypeptide includes functional fragments of the polypeptide, as long as the activity of GDF-10 remains. Small peptides containing the biological activity of GDF-10 are included in he invention.

The invention provides polynucleotides encoding the GDF-10 protein. These polynucleotides include DNA, cDNA and RNA sequences which encode GDF-10. It is understood that all polynucleotides encoding all or a portion of GDF-10 are also included herein, as long as they encode a polypeptide with GDF-10 activity. Such polynucleotides include naturally occurring, synthetic, and intentionally manipulated polynucleotides. For example, GDF-10 polynucleotide may be subjected to site-directed mutagenesis. The polynucleotide sequence for GDF-10 also includes antisense sequences. The polynucleotides of the invention include sequences that are degenerate as a result of the genetic code. There are 20 natural amino acids, most of which are specified by more than one codon. Therefore, a degenerate nucleotide sequences are included in the invention as long as the amino acid sequence of GDF-10 polypeptide encoded by the nucleotide sequence is functionally unchanged.

Specifically disclosed herein is a cDNA sequence for GDF-10 which is 2322 base pairs in length and contain an open reading frame beginning with a methionine codon at nucleotide 126. The encoded polypeptide is 476 amino acids in length with a molecular weight of about 52.5 kD, as determined by nucleotide sequence analysis. The GDF-10 sequence contains a core of hydrophobic amino acids near the N-terminus, suggestive of a signal sequence for secretion. GDF-10 contains four potential N-glycosylation sites tasparagine residues 114, 152, 277, and 467. GDF-10 contains several potential proteolytic processing sites. Cleavage most likely occurs following arginine 365, which would generate a mature fragment of DF-10 predicted to be 111 amino acids in length and have an unglycosylated molecular weight of about 12.6 kD, as determined by nucleotide sequence analysis. One skilled in the art can modify, or partially or completely remove, the glycosyl groups from the GDF-10 protein using standard techniques. Therefore the functional protein or fragments thereof of the invention includes glycosylated, partially glycosylated and unglycosylated species of GDF-10.

The C-terminal region of GDF-10 following the putative proteolytic processing site shows significant homology to the known members of the TGF-β superfamily. The GDF-10 sequence contains most of the residues that are highly conserved in other family members. Among the known family mammalian TGF-β family members, GDF-10 is most homologous to BMP-3 (83% sequence identity beginning with the first conserved cysteine residue). GDF-10 also shows significant homology to BMP-3 (approximately 30% sequence identity) in the pro-region of the molecule. Based on these sequence comparisons, GDF-10 and BMP-3 appear to define a new subfamily within the larger superfamily.

Minor modifications of the recombinant GDF-10 primary amino acid sequence may result in proteins which have substantially equivalent activity as compared to the GDF-10 polypeptide described herein. Such modifications may be deliberate, as by site-directed mutagenesis, or may be spontaneous. All of the polypeptides produced by these modifications are included herein as long as the biological activity of GDF-10 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-10 bilogical activity.

The nucleotide sequence encoding the GDF-10 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginin for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-10 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogene us mixture of denatured double-stranded DNA. For such screening, hybridization is preferably performed on either single-stranded DNA ordenatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

The development of specific DNA sequence, encoding GDF-10 can also be obtained by: 1) isolation of double-stranded DNA sequences from the genomic DNA; 2) chemical manufacture of DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lamb a gt11, can be screened indirectly for GDF-10 peptides having at least one epitope, using antibodies specific for GDF-10. Such antibodies can be either polyconally or monoclonally derived and used to detect expression product indicative of the presence of GDF-10 cDNA.

DNA sequences encoding GDF-10 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-10 polynucleotide sequences may be inserted into a recombinant expression vector. The term "recombinant expression vector" refers to a plasmid, virus or other vehicle known in the art that has been manipulated by insertion or incorporation of the GDF-10 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-10 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of DF-10 is expressed from a cDNA clone containing the entire coding sequence of GDF-10. Alternatively, the C-terminal portion of GDF-10 can be expressed as a fusion protein with the pro- region of another member of the TGF-β family or co-expressed with another pro- region (see for example, Hammonds, et al., *Molec. Endocrin.* 5:149, 1991; Gray, A., and Mason, A., *Science,* 247:1328, 1990).

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequent treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-10 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, Eukaryotic Viral Vectors, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-10 polypeptide or functional fragments thereof. Antibody which consists essentially of pooled monoclonal antibodies with different epitopic specificities, as well as distinct monoclonal antibody preparations are provided. Monoclonal antibodies are mad from antigen containing fragments of the protein by methods well known to those skilled in the art (Kohler, et al., *Nature,* 256:495, 1975). The term antibody as used in this invention is meant to include intact molecules as well as fragments thereof, such as Fab and $F(ab')_2$ which are capable of binding an epitopic determinant on GDF-10.

The term "cell-proliferative disorder" denote malignant as well as non-malignant cell populations which often appear to differ from the surrounding tissue both morphologically an genotypically. The term "cell-proliferative disorder" also includes situations in which a normally occurring process could be enhanced or suppressed for clinical benefit; an example of such a process would be fracture healing. Malignant cells (i.e. cancer) develop as a result of a multi-step process. The GDF-10 polynucleotide that is an antisense molecule is useful in treating malignancies of the various organ systems, particularly, for example, cells in uterine or adipose tissue. Essentially, any disorder which is etiologically linked to altered expression of GF-10 could be considered susceptible to treatment with a GDF-10 suppressing reagent. One such disorder is a malignant cell proliferative disorder, for example.

The invention provides a method for detecting a cell proliferative disorder of uterine or adipose tissue which comprises contacting an anti-GDF-10 antibody with a cell suspected of having a GDF-10 associated disorder and detecting binding to the antibody. The antibody reactive with GDF-10 is labeled with a compound which allows detection of binding to GDF-10. For purposes of the invention, an antibody specific for GDF-10 polypeptide may be used to detect the level of GDF-10 in biological fluids and tissues. An specimen containing a detectable amount of antigen can be used. A preferred sample of this invention is uterine or fat tissue. The level of GDF-10 in the suspect cell can be compared with the level in a normal cell to determine whether the subject has a GDF-10-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. These skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylentriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and 56Fe.

The monoclonal antibodies of the invention can be used in vitro and in vivo to monitor the course of amelioration of a GDF-10-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-10-associated disease is effective. The term "ameliorate" denotes a lessening of the detrimental effect of the GDF-10-associated disease in the subject receiving therapy.

The present invention identifies a nucleotic be sequence that can be expressed in an altered manner as compared to expression in a normal cell, therefore it is possible to design appropriate therapeutic or diagnostic techniques directed to this sequence. Thus, where a cell-proliferative disorder is associated with the expression of GDF-10, nucleic acid sequences that interfere with GDF-10 expression at the translational level can be used. This approach utilizes, for example, antisense nucleic acid and ribozymes to block translation of a specific GDF-10 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, Scientific American, 262:40, 1 990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-10-producing cell. The use of antisense methods to inhibit the in vitro translation of genes is well known in the art (Marcus-Sakura, Anal. Biochem., 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes or inactivating a specific mRNA species and 18-based recognition sequences are preferable to shorter recognition sequences.

The present invention also provides gene therapy for the treatment of cell proliferative disorders which are mediated by GDF-10 protein. Such therapy would achieve its therapeutic effect by introduction of the GDF-10 antisense polynucleotide into cells having the proliferative disorder. Delivery of antisense GDF-10 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-10 sequence of interest into the viral vector, along with another gene which encodes the ligand for a receptor on a specific target cell, or example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GDF-10 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-10 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-10 primarily in uterine and adipose tissue, there are a variety of applications using the polypeptide, polynucleotide, and antibodies of the invention, related to these and other tissues. Such applications include treatment of cell proliferative disorders involving these and other tissues, including bone. In addition, GDF-10 may be useful in various gene therapy procedures.

The following examples are intended to illustrate but not limit the invention. While they are typical of those that might be used, other procedures known to those skilled in the art may alternatively be used.

EXAMPLE 1 IDENTIFICATION AND ISOLATION OF A NOVEL TGF-β FAMILY MEMBER

To identify new members of the TGF-β superfamily, degenerate oligonucleotides were designed which corresponded to two conserved regions among the known family members: one region downstream of the first conserved cysteine residue and the other region spanning the invariant cysteine residues near the C-terminus. These primers were used for polymerase chain reactions on lung and brain cDNA followed by subcloning the PCR products using restriction sites placed at the 5' ends of the primers, picking individual *E. coli* colonies carrying these subcloned inserts, and using a combination of random sequencing and hybridization analysis to eliminate know members of the superfamily.

GDF-10 was identified from a mixture of PCR products obtained with the primers:

```
NSC1: 5'-
CCGGAATTCAA(G/A)GT(G/A/T/C)GA(T/C)TT(T/C)GC(G/A/T/C)GA (T/C)AT(A/C/T)GG(G/A/T/C)TGG-3'  (SEQ ID NO:1)

NSC2: 5'-
CCGGMTTC(A/G)CA(G/A/T/C)GC(A/G)CA(G/A)CT(T/C)TC(G/A/T/C)

AC(G/A/T/C)GTCAT-3'  (SEQ ID NO:2)

NSC3: 5'-
CCGGAATTC(A/G)CA(G/A/T/C)GC(A/G)CA(G/A/T/C)GA(T/C)TC (G/A/T/C)AC(G/A/T/C)GTCA-3'  (SEQ ID NO:3)
```

PCR using primers NSC1 with NSC2 or NSC1 with NSC3 was carried out with cDNA prepared from 0.25 μg of lung or brain mRNA for 35 cycles at 94° C. for 1 min, 50° C. for 2 min, and 72° C. for 2 min. PCR products of approximately 300 base pairs were digested with Eco RI, gel purified, and subcloned in the Bluescript vector (Stratagene, San Diego, Calif.). DNA was prepared from bacterial colonies carrying individual subclones and sequenced. Of 11 clone that were sequenced, 9 corresponded to BMP-3, and two represented a novel sequence, which was designated GDF-10.

EXAMPLE 2 EXPRESSION PATTERN AND SEQUENCE OF GDF-10

To determine the expression pattern of GDF-10, RNA samples prepared from a variety of adult tissues were screened by Northern analysis. 2.5 micrograms of twice polyA-selected RNA prepared from each tissue were electrophoresed on formaldehyde gels, blotted and probed with GDF-10. As shown in FIG. 1, the GDF-10 probe detected an mRNA expressed at highest levels in uterus, fat, and brain.

A murine uterus cDNA library consisting of $3 \times 10^6$ recombinant phage was constructed in lambda ZAP II and screened with a probe derived from the GDF-10 PCR product. The entire nucleotide sequence of the longest of 7 hybridizing clones is shown in FIG. 2. Consensus N-glycosylation signals are denoted by plain boxes. Numbers indicate nucleotide position relative to the 5' end. The 2322 bp sequence contains a long open reading frame beginning with a methionine codon at nucleotide 126 and potentially encoding a protein 476 amino acids in length with a molecular weight of 52.5 kD. The predicted GDF-10 amino acid sequence contains a hydrophobic N-terminal region, suggestive of a signal sequence for secretion, four potential N-linked glycosylation sites at asparagine residues 11, 152, 277, and 467 and a putative proteolytic processing site at amino acid 365. Cleavage of the GDF-10 precursor at this site would generate a mature GDF-10 protein 111 amino acids in length with a predicted unglycosylated molecular weight of 12.6 kD.

The C-terminal region of GDF-10 following the putative proteolytic processing site shows significant homology to the known members of the TGF-β superfamily (FIG. 3). FIG. 3 shows the alignment of the C-terminal sequences of GDF-10 with the corresponding regions of human GDF-1 (Lee, Proc. Natl. Acad. Sci. USA, 88:4250–4254, 1991), murine GDF-3 and GDF-9 (McPherron and Lee, J. Biol. Chem. 268:3444, 1993), human BMP-2 and 4 (Wozney, et al., Science, 242:1528–1534, 1988), human Vgr-1 (Celeste, et al., Proc. Natl. Acad. Sci. USA, 87:9843–9847, 1990), human OP-1 (Ozkaynak, et al., EMBO J., 9:2085–2093, 1990), human BMP-5 (Celeste, et al., Proc. Natl. Acad. Sci. USA, 87:9843–9847, 1990), human OP-2 (Ozkaynak, et al., J. Biol. Chem., 267:25220–25227, 1992), human BMP-3 (Wozney, et al., Science, 242:1528–1534, 1988), human MIS (Cate, et al., Cell, 45:685–698, 1986), human inhibin alpha, βA, and, βB (Mason, et al., Biochem, Biophys. Res. Commun., 135:957–964, 1986), murine nodal (Zhou, et al., Nature, 361:543–547, 1993), human TGF-β1 (Derynck, et al., Nature, 316:701–705,1985), human TGF-β2 (deMartin, et al., EMBO J., 6:3673–3677, 1987), and human TGF-β3 (ten Dijke, et al., Proc. Natl. Acad. Sci. USA, 85:4715–4719, 1988). The conserved cysteine residues are boxed. Dashes denote gaps introduced in order to maximize the alignment.

GDF-10 contains most of the residues that are highly conserved in other family members, including the seven cysteine residues with their characteristic spacing.

FIG. 4 shows the amino acid homologies among the different members of the TGF-β superfamily. Numbers represent percent amino acid identities calculated from the first conserved cysteine to the C-terminus. In this region, GDF-10 is most homologous to BMP-3 (83% sequence identity).

EXAMPLE 3 ISOLATION OF HUMAN GDF-10

To isolate human GDF-10, a human uterus cDNA library consisting of $16.2 \times 10^6$ recombinant phage was constructed in lambda ZAP II and screened with a murine GDF-10 probe. From this library, 20 hybridizing clones were isolated. Partial nucleotide sequence analysis of the longest clone showed that human and murine GDF-10 are highly homologous; the predicted amino acid sequences are 97% identical beginning with the first conserved cysteinie residue following the predicted cleavage site (FIG. 5).

EXAMPLE 4 SECRETION OF GDF-10 BY MAMMALIAN CELLS

To determine whether GDF-10 is secreted by mammalian cells, the GDF-10 cDNA was cloned into the pcDNAI expression vector and transfected into 293 cells. Following DNA transfection, the cells were metabolically labeled with a mixture of [$^{35}$S]-cysteine and [$^{35}$S]-methionine, and labeled secreted proteins were analyzed by SDS-polyacrylamide gel electrophoresis. As show in FIG. 6, additional bands were detected in cells transfected with a sense GDF-10 construct compared to an antisense control construct. The presence of multiple protein species most likely indicates that 293 cells are capable of proteolytically processing GDF-10. Hence, these data suggest that GDF-10 is secreted by these cells and that GDF-10 is cleaved, as predicted from the cDNA sequence.

Although the invention has been described with reference to the presently preferred embodiment, it should be understood that various modifications can be made without departing from the spirit of the invention. Accordingly, the invention is limited only by the following claims.

What is claimed is:

1. Substantially pure growth differentiation factor-10 (GDF-10) having the amino acid sequence as set forth in SEQ ID NO:5 or SEQ ID NO:25.

2. An isolated polynucleotide encoding GDF-10 polypeptide having the amino acid sequence as set forth in SEQ ID NO:5 or SEQ ID NO:25.

3. The polynucleotide of claim 2, wherein the polynucleotide is isolated from a mammalian cell.

4. The polynucleotide of claim 3, wherein the mammalian cell is selected from the group consisting of a mouse, rat, and human cell.

5. An expression vector comprising the polynucleotide of claim 2.

6. The vector of claim 5, wherein the vector is a plasmid.

7. The vector of claim 5, wherein the vector is a viral vector.

8. A host cell containing the vector of claim 5.

9. The host cell of claim 8, wherein the cell is prokaryotic.

10. The host cell of claim 8, wherein the cell is eukaryotic.

11. An isolated polynucleotide selected from the group consisting of:

a) SEQ ID NO:4;

b) SEQ ID NO:4, wherein T can also be U;

c) nucleic acid sequences complementary to SEQ ID NO:4 and d) fragments of a), b), or c) that are at least 15 bases in length and that will hybridize to genomic DNA which encodes the GDF-10 protein of SEQ ID NO:5 or SEQ ID NO: 25.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: NSC1

(ix) FEATURE:
       (A) NAME/KEY: CDS
       (B) LOCATION: 1..36

(xi) SEQUENCE DESCRIPTION: SEQ ID NO:1:

CCGGAATTCA ARGTNGAYTT YGCNGAYATH GGNTGG                              36

(2) INFORMATION FOR SEQ ID NO:2:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: NSC2

(ix) FEATURE:
       (A) NAME/KEY: CDS
       (B) LOCATION: 1..33

(xi) SEQUENCE DESCRIPTION: SEQ ID NO:2:

CCGGAATTCR CANGCRCARC TYTCNACNGT CAT                                 33

(2) INFORMATION FOR SEQ ID NO:3:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: NSC3

(ix) FEATURE:
       (A) NAME/KEY: CDS
       (B) LOCATION: 1..33

(xi) SEQUENCE DESCRIPTION: SEQ ID NO:3:

CCGGAATTCR CANGCRCANG AYTCNACNGT CAT                                 33

(2) INFORMATION FOR SEQ ID NO:4:

(i) SEQUENCE CHARACTERISTICS:
       (A) LENGTH: 2322 base pairs
       (B) TYPE: nucleic acid -continued

```
        (C) STRANDEDNESS: single
        (D) TOPOLOGY: linear (ii) MOLECULE TYPE: DNA (genomic)

(vii) IMMEDIATE SOURCE:
        (B) CLONE: Murine GDF-10

(ix) FEATURE:
        (A) NAME/KEY: CDS
        (B) LOCATION: 126..1553

(xi) SEQUENCE DESCRIPTION: SEQ ID NO:4:

TGGGGTCATC CGGGCTGTCC GAGTCCCACA GGGACAACTC CAGCCGCGGA CGAGGTGCAC      60

AGCCAACACT GAGCCCTCCT TGTCTGTTCT CCTGGGCTCA GACCCTTCAC CACCGTTACT    120

CAGCC ATG GCT CCA GGT CCT GCT CGG ATC AGC TTG GGG TCC CAG CTG        167
      Met Ala Pro Gly Pro Ala Arg Ile Ser Leu Gly Ser Gln Leu
        1               5                  10

CTG CCC ATG GTG CCG CTG CTC CTG CTG CTG CGG GGC GCA GGC TGC GGC      215
Leu Pro Met Val Pro Leu Leu Leu Leu Leu Arg Gly Ala Gly Cys Gly
 15              20                  25                  30

CAC AGG GGC CCC TCA TGG TCC TCA TTG CCC TCG GCA GCT GCC GGT CTG      263
His Arg Gly Pro Ser Trp Ser Ser Leu Pro Ser Ala Ala Ala Gly Leu
                 35                  40                  45

CAG GGG GAC AGG GAC TCC CAG CAG TCA CCC GGG GAC GCA GCA GCC GCT      311
Gln Gly Asp Arg Asp Ser Gln Gln Ser Pro Gly Asp Ala Ala Ala Ala
             50                  55                  60

CTG GGC CCA GGC GCC CAG GAC ATG GTC GCT ATC CAC ATG CTC AGG CTC      359
Leu Gly Pro Gly Ala Gln Asp Met Val Ala Ile His Met Leu Arg Leu
         65                  70                  75

TAT GAG AAG TAC AAC CGA AGA GGT GCT CCA CCG GGA GGA GGC AAC ACC      407
Tyr Glu Lys Tyr Asn Arg Arg Gly Ala Pro Pro Gly Gly Gly Asn Thr
 80                  85                  90

GTC CGA AGC TTC CGT GCC CGG CTG GAA ATG ATC GAC CAA AAG CCT GTG      455
Val Arg Ser Phe Arg Ala Arg Leu Glu Met Ile Asp Gln Lys Pro Val
 95                 100                 105                 110

TAT TTC TTC AAC TTG ACT TCC ATG CAA GAC TCA GAA ATG ATC CTC ACA      503
Tyr Phe Phe Asn Leu Thr Ser Met Gln Asp Ser Glu Met Ile Leu Thr
                115                 120                 125

GCC GCC TTC CAC TTC TAC TCA GAA CCT CCA CGG TGG CCC CGG GCT GGT      551
Ala Ala Phe His Phe Tyr Ser Glu Pro Pro Arg Trp Pro Arg Ala Gly
            130                 135                 140

GAG GTA TTC TGC AAG CCC CGA GCT AAG AAC GCA TCC TGC CGC CTC CTG      599
Glu Val Phe Cys Lys Pro Arg Ala Lys Asn Ala Ser Cys Arg Leu Leu
        145                 150                 155

ACC CCA GGG CTG CCT GCA CGC TTG CAC CTA ATC TTC CGC AGT CTT TCC      647
Thr Pro Gly Leu Pro Ala Arg Leu His Leu Ile Phe Arg Ser Leu Ser
    160                 165                 170

CAG AAC ACC GCC ACT CAG GGG CTG CTC CGC GGG GCC ATG GCC CTG ACG      695
Gln Asn Thr Ala Thr Gln Gly Leu Leu Arg Gly Ala Met Ala Leu Thr
175                 180                 185                 190

CCT CCA CCA CGT GGC CTG TGG CAG GCC AAG GAC ATC TCC TCA ATC ATC      743
Pro Pro Pro Arg Gly Leu Trp Gln Ala Lys Asp Ile Ser Ser Ile Ile
                195                 200                 205

AAG GCT GCC CGA AGG GAT GGA GAG CTG CTT CTC TCT GCT CAG CTG GAT      791
Lys Ala Ala Arg Arg Asp Gly Glu Leu Leu Leu Ser Ala Gln Leu Asp
            210                 215                 220

ACT GGG GAG AAG GAC CCC GGA GTG CCA CGG CCC AGT TCC CAC ATG CCC      839
Thr Gly Glu Lys Asp Pro Gly Val Pro Arg Pro Ser Ser His Met Pro
        225                 230                 235

TAT ATC CTT GTC TAC GCC AAT GAC CTG GCC ATC TCC GAA CCC AAC AGT      887
```

```
Tyr Ile Leu Val Tyr Ala Asn Asp Leu Ala Ile Ser Glu Pro Asn Ser
    240                 245                 250

GTA GCA GTG TCG CTA CAG AGA TAC GAC CCA TTT CCA GCT GGA GAC TTT        935
Val Ala Val Ser Leu Gln Arg Tyr Asp Pro Phe Pro Ala Gly Asp Phe
255                 260                 265                 270

GAG CCT GGA GCA GCC CCC AAC AGC TCA GCT GAT CCC CGC GTG CGC AGG        983
Glu Pro Gly Ala Ala Pro Asn Ser Ser Ala Asp Pro Arg Val Arg Arg
                275                 280                 285

GCG GCT CAG GTG TCA AAA CCC CTG CAA GAC AAT GAA CTG CCG GGG CTG       1031
Ala Ala Gln Val Ser Lys Pro Leu Gln Asp Asn Glu Leu Pro Gly Leu
            290                 295                 300

GAT GAA AGA CCA GCG CCT GCC CTG CAT GCC CAG AAT TTC CAC AAG CAC       1079
Asp Glu Arg Pro Ala Pro Ala Leu His Ala Gln Asn Phe His Lys His
        305                 310                 315

GAG TTC TGG TCC AGT CCT TTC CGG GCA CTG AAA CCC CGC ACG GCG CGC       1127
Glu Phe Trp Ser Ser Pro Phe Arg Ala Leu Lys Pro Arg Thr Ala Arg
320                 325                 330

AAA GAC CGC AAG AAG AAG GAC CAG GAC ACA TTC ACC GCC GCC TCC TCT       1175
Lys Asp Arg Lys Lys Lys Asp Gln Asp Thr Phe Thr Ala Ala Ser Ser
335                 340                 345                 350

CAG GTG CTG GAC TTT GAC GAG AAG ACG ATG CAG AAA GCC AGG AGG CGG       1223
Gln Val Leu Asp Phe Asp Glu Lys Thr Met Gln Lys Ala Arg Arg Arg
                355                 360                 365

CAG TGG GAT GAG CCC CGG GTC TGC TCC AGG AGG TAC CTG AAG GTG GAT       1271
Gln Trp Asp Glu Pro Arg Val Cys Ser Arg Arg Tyr Leu Lys Val Asp
            370                 375                 380

TTT GCA GAC ATC GGG TGG AAT GAA TGG ATC ATC TCT CCC AAA TCC TTT       1319
Phe Ala Asp Ile Gly Trp Asn Glu Trp Ile Ile Ser Pro Lys Ser Phe
        385                 390                 395

GAC GCC TAC TAC TGT GCT GGG GCC TGC GAG TTC CCC ATG CCC AAG ATT       1367
Asp Ala Tyr Tyr Cys Ala Gly Ala Cys Glu Phe Pro Met Pro Lys Ile
400                 405                 410

GTC CGC CCA TCC AAC CAT GCC ACC ATC CAG AGC ATC GTC AGA GCT GTG       1415
Val Arg Pro Ser Asn His Ala Thr Ile Gln Ser Ile Val Arg Ala Val
415                 420                 425                 430

GGC ATT GTC CCT GGC ATC CCA GAG CCA TGC TGT GTT CCA GAC AAG ATG       1463
Gly Ile Val Pro Gly Ile Pro Glu Pro Cys Cys Val Pro Asp Lys Met
                435                 440                 445

AAC TCC CTT GGA GTC CTT TTC CTG GAT GAA AAT CGG AAT GCG GTT CTG       1511
Asn Ser Leu Gly Val Leu Phe Leu Asp Glu Asn Arg Asn Ala Val Leu
            450                 455                 460

AAG GTG TAC CCC AAT ATG TCC GTA GAG ACC TGT GCC TGT CGG               1553
Lys Val Tyr Pro Asn Met Ser Val Glu Thr Cys Ala Cys Arg
        465                 470                 475

TAAGATGGCT TCAAGATAGA AGACAGACCT GCTTCATCCC TGCCCTGCAG AGTGGCAATC    1613

TTGGAGCCAG GGACTTGACT CGGGGAGGTT CCAGGTGCTA GACAGAGCTT ACAGGCAGCC    1673

CTGCTGGGAC CAAGAAAGAT CTGCCCACCA CATCGCAATT CTTCAGTTCT TCCGTGCTGG    1733

TGGTAGCTCT GTAAAGACGT GTTGAGTTCC TGGAAGAAAT CTGGAATTAA CTGTGGTCTG    1793

CAATTTGCCC ATCATCCCTG CCCACACTTT TCAAGGCCTA GAAATAACGT GTGTCCTCAA    1853

ATGTCAACTC CAGGCATTTG TCCTCTCAAA ACCTAGAAAG ACTATGCAAA TCTTGGGGTA    1913

CTCCCCCCCC CCATGGCAGT TTAAATGCTG TTTTAAAACC CTCAGGCTGC ATTCTAGAAA    1973

CAGGGCCTAA CCCATGGCAC GAGTGAGTAT TTTCTCTTAC GTTTCACTAC ACGTGCTTTT    2033

ATACATGCAG TATGCACATG TAATCACGGT TGATTTCTTC TTTTAATATA TGTATTTCTA    2093

TTTCAAAGCA AAACGGAGAG AGTCGATCCC ATCCCCTGCA GAGGTAATAA TGCAAGTTAG    2153
```

```
GTGTGGGTTG TCTAAGCATG TGTATGGAAA TAATACATAC AGTAATATGC TGGAATACTA    2213

AAAAAGTAAC CAAGATTTTA TATTTTTGTA AATTATACTT TGTATACTGT AGATTGTGAG    2273

TGTTCTGTGT TTTTATGGAA AGCTAATAAA TTAAAGGTGC GGAGGTATC                2322
```

(2) INFORMATION FOR SEQ ID NO:5:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ala Pro Gly Pro Ala Arg Ile Ser Leu Gly Ser Gln Leu Leu Pro
 1               5                  10                  15

Met Val Pro Leu Leu Leu Leu Arg Gly Ala Gly Cys Gly His Arg
                20                  25                  30

Gly Pro Ser Trp Ser Ser Leu Pro Ser Ala Ala Ala Gly Leu Gln Gly
                35                  40                  45

Asp Arg Asp Ser Gln Gln Ser Pro Gly Asp Ala Ala Ala Leu Gly
    50                  55                  60

Pro Gly Ala Gln Asp Met Val Ala Ile His Met Leu Arg Leu Tyr Glu
65                  70                  75                  80

Lys Tyr Asn Arg Arg Gly Ala Pro Pro Gly Gly Gly Asn Thr Val Arg
                85                  90                  95

Ser Phe Arg Ala Arg Leu Glu Met Ile Asp Gln Lys Pro Val Tyr Phe
                100                 105                 110

Phe Asn Leu Thr Ser Met Gln Asp Ser Glu Met Ile Leu Thr Ala Ala
                115                 120                 125

Phe His Phe Tyr Ser Glu Pro Pro Arg Trp Pro Arg Ala Gly Glu Val
                130                 135                 140

Phe Cys Lys Pro Arg Ala Lys Asn Ala Ser Cys Arg Leu Leu Thr Pro
145                 150                 155                 160

Gly Leu Pro Ala Arg Leu His Leu Ile Phe Arg Ser Leu Ser Gln Asn
                165                 170                 175

Thr Ala Thr Gln Gly Leu Leu Arg Gly Ala Met Ala Leu Thr Pro Pro
                180                 185                 190

Pro Arg Gly Leu Trp Gln Ala Lys Asp Ile Ser Ser Ile Ile Lys Ala
                195                 200                 205

Ala Arg Arg Asp Gly Glu Leu Leu Ser Ala Gln Leu Asp Thr Gly
    210                 215                 220

Glu Lys Asp Pro Gly Val Pro Arg Pro Ser Ser His Met Pro Tyr Ile
225                 230                 235                 240

Leu Val Tyr Ala Asn Asp Leu Ala Ile Ser Glu Pro Asn Ser Val Ala
                245                 250                 255

Val Ser Leu Gln Arg Tyr Asp Pro Phe Pro Ala Gly Asp Phe Glu Pro
                260                 265                 270

Gly Ala Ala Pro Asn Ser Ser Ala Asp Pro Arg Val Arg Arg Ala Ala
                275                 280                 285

Gln Val Ser Lys Pro Leu Gln Asp Asn Glu Leu Pro Gly Leu Asp Glu
                290                 295                 300

Arg Pro Ala Pro Ala Leu His Ala Gln Asn Phe His Lys His Glu Phe
305                 310                 315                 320

Trp Ser Ser Pro Phe Arg Ala Leu Lys Pro Arg Thr Ala Arg Lys Asp
```

-continued

```
                  325                 330                 335
Arg Lys Lys Lys Asp Gln Asp Thr Phe Thr Ala Ala Ser Ser Gln Val
            340                 345                 350

Leu Asp Phe Asp Glu Lys Thr Met Gln Lys Ala Arg Arg Arg Gln Trp
            355                 360                 365

Asp Glu Pro Arg Val Cys Ser Arg Arg Tyr Leu Lys Val Asp Phe Ala
    370                 375                 380

Asp Ile Gly Trp Asn Glu Trp Ile Ile Ser Pro Lys Ser Phe Asp Ala
385                 390                 395                 400

Tyr Tyr Cys Ala Gly Ala Cys Glu Phe Pro Met Pro Lys Ile Val Arg
                405                 410                 415

Pro Ser Asn His Ala Thr Ile Gln Ser Ile Val Arg Ala Val Gly Ile
            420                 425                 430

Val Pro Gly Ile Pro Glu Pro Cys Cys Val Pro Asp Lys Met Asn Ser
            435                 440                 445

Leu Gly Val Leu Phe Leu Asp Glu Asn Arg Asn Ala Val Leu Lys Val
    450                 455                 460

Tyr Pro Asn Met Ser Val Glu Thr Cys Ala Cys Arg
465                 470                 475
```

(2) INFORMATION FOR SEQ ID NO:6:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-10

(ix) FEATURE:
        (A) NAME/KEY: Protein
        (B) LOCATION: 1..120

(xi) SEQUENCE DESCRIPTION: SEQ ID NO:6:

```
Glu Lys Ser Met Gln Lys Ala Arg Arg Arg Gln Trp Asp Glu Pro Arg
1               5                   10                  15

Val Cys Ser Arg Arg Tyr Leu Lys Val Asp Phe Ala Asp Ile Gly Trp
            20                  25                  30

Asn Glu Trp Ile Ile Ser Pro Lys Ser Phe Asp Ala Tyr Tyr Cys Ala
            35                  40                  45

Gly Ala Cys Glu Phe Pro Met Pro Lys Ile Val Arg Pro Ser Asn His
50                  55                  60

Ala Thr Ile Gln Ser Ile Val Arg Ala Val Gly Ile Val Pro Gly Ile
65                  70                  75                  80

Pro Glu Pro Cys Cys Val Pro Asp Lys Met Asn Ser Leu Gly Val Leu
                85                  90                  95

Phe Leu Asp Glu Asn Arg Asn Ala Val Leu Lys Val Tyr Pro Asn Met
            100                 105                 110

Ser Val Glu Thr Cys Ala Cys Arg
            115                 120
```

(2) INFORMATION FOR SEQ ID NO:7:

(i) SEQUENCE CHARACTERISTICS:
        (A) LENGTH: 123 amino acids
        (B) TYPE: amino acid (C) STRANDEDNESS: single
        (D) TOPOLOGY: linear (ii) MOLECULE TYPE: protein (vii) IMMEDIATE SOURCE:
        (B) CLONE: GDF-1

(ix) FEATURE:
        (A) NAME/KEY: Protein
        (B) LOCATION: 1..123

(xi) SEQUENCE DESCRIPTION: SEQ ID NO:7:

Arg Pro Arg Arg Asp Ala Glu Pro Val Leu Gly Gly Pro Gly Gly
1               5                   10                  15

Ala Cys Arg Ala Arg Arg Leu Tyr Val Ser Phe Arg Glu Val Gly Trp
            20                  25                  30

His Arg Trp Val Ile Ala Pro Arg Gly Phe Leu Ala Asn Tyr Cys Gln
            35                  40                  45

Gly Gln Cys Ala Leu Pro Val Ala Leu Ser Gly Ser Gly Gly Pro Pro
        50                  55                  60

Ala Leu Asn His Ala Val Leu Arg Ala Leu Met His Ala Ala Ala Pro
65                  70                  75                  80

Gly Ala Ala Asp Leu Pro Cys Cys Val Pro Ala Arg Leu Ser Pro Ile
                85                  90                  95

Ser Val Leu Phe Phe Asp Asn Ser Asp Asn Val Val Leu Arg Gln Tyr
                100                 105                 110

Glu Asp Met Val Val Asp Glu Cys Gly Cys Arg
            115                 120

(2) INFORMATION FOR SEQ ID NO:8:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-3

(ix) FEATURE:
        (A) NAME/KEY: Protein
        (B) LOCATION: 1..118

(xi) SEQUENCE DESCRIPTION: SEQ ID NO:8:

Arg Lys Arg Arg Ala Ala Ile Ser Val Pro Lys Gly Phe Cys Arg Asn
1               5                   10                  15

Phe Cys His Arg His Gln Leu Phe Ile Asn Phe Gln Asp Leu Gly Trp
            20                  25                  30

His Lys Trp Val Ile Ala Pro Lys Gly Phe Met Ala Asn Tyr Cys His
            35                  40                  45

Gly Glu Cys Pro Phe Ser Met Thr Thr Tyr Leu Asn Ser Ser Asn Tyr
        50                  55                  60

Ala Phe Met Gln Ala Leu Met His Met Ala Asp Pro Lys Val Pro Lys
65                  70                  75                  80

Ala Val Cys Val Pro Thr Lys Leu Ser Pro Ile Ser Met Leu Tyr Gln
                85                  90                  95

Asp Ser Asp Lys Asn Val Ile Leu Arg His Tyr Glu Asp Met Val Val
                100                 105                 110

```
Asp Glu Cys Gly Cys Gly
        115

(2) INFORMATION FOR SEQ ID NO:9:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
         (B) CLONE: GDF-9

(ix) FEATURE:
         (A) NAME/KEY: Protein
         (B) LOCATION: 1..119

(xi) SEQUENCE DESCRIPTION: SEQ ID NO:9:

Ser Phe Asn Leu Ser Glu Tyr Phe Lys Gln Phe Leu Phe Pro Gln Asn
1               5                   10                  15

Glu Cys Glu Leu His Asp Phe Arg Leu Ser Phe Ser Gln Leu Lys Trp
            20                  25                  30

Asp Asn Trp Ile Val Ala Pro His Arg Tyr Asn Pro Arg Tyr Cys Lys
        35                  40                  45

Gly Asp Cys Pro Arg Ala Val Arg His Arg Tyr Gly Ser Pro Val His
    50                  55                  60

Thr Met Val Gln Asn Ile Ile Tyr Glu Lys Leu Asp Pro Ser Val Pro
65                  70                  75                  80

Arg Pro Ser Cys Val Pro Gly Lys Tyr Ser Pro Leu Ser Val Leu Thr
                85                  90                  95

Ile Glu Pro Asp Gly Ser Ile Ala Tyr Lys Glu Tyr Glu Asp Met Ile
            100                 105                 110

Ala Thr Arg Cys Thr Cys Arg
        115

(2) INFORMATION FOR SEQ ID NO:10:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
         (B) CLONE: BMP-2

(ix) FEATURE:
         (A) NAME/KEY: Protein
         (B) LOCATION: 1..118

(xi) SEQUENCE DESCRIPTION: SEQ ID NO:10:

Arg Glu Lys Arg Gln Ala Lys His Lys Gln Arg Lys Arg Leu Lys Ser
1               5                   10                  15

Ser Cys Lys Arg His Pro Leu Tyr Val Asp Phe Ser Asp Val Gly Trp
            20                  25                  30

Asn Asp Trp Ile Val Ala Pro Pro Gly Tyr His Ala Phe Tyr Cys His
        35                  40                  45

Gly Glu Cys Pro Phe Pro Leu Ala Asp His Leu Asn Ser Thr Asn His
    50                  55                  60
```

```
Ala Ile Val Gln Thr Leu Val Asn Ser Val Asn Ser Lys Ile Pro Lys
 65                  70                  75                  80

Ala Cys Cys Val Pro Thr Glu Leu Ser Ala Ile Ser Met Leu Tyr Leu
                 85                  90                  95

Asp Glu Asn Glu Lys Val Val Leu Lys Asn Tyr Gln Asp Met Val Val
            100                 105                 110

Glu Gly Cys Gly Cys Arg
        115
```

(2) INFORMATION FOR SEQ ID NO:11:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: BMP-4

(ix) FEATURE:
        (A) NAME/KEY: Protein
        (B) LOCATION: 1..118

(xi) SEQUENCE DESCRIPTION: SEQ ID NO:11:

```
Lys Arg Ser Pro Lys His His Ser Gln Arg Ala Arg Lys Lys Asn Lys
 1               5                  10                  15

Asn Cys Arg Arg His Ser Leu Tyr Val Asp Phe Ser Asp Val Gly Trp
                 20                  25                  30

Asn Asp Trp Ile Val Ala Pro Pro Gly Tyr Gln Ala Phe Tyr Cys His
             35                  40                  45

Gly Asp Cys Pro Phe Pro Leu Ala Asp His Leu Asn Ser Thr Asn His
         50                  55                  60

Ala Ile Val Gln Thr Leu Val Asn Ser Val Asn Ser Ser Ile Pro Lys
 65                  70                  75                  80

Ala Cys Cys Val Pro Thr Glu Leu Ser Ala Ile Ser Met Leu Tyr Leu
                 85                  90                  95

Asp Glu Tyr Asp Lys Val Val Leu Lys Asn Tyr Gln Glu Met Val Val
            100                 105                 110

Glu Gly Cys Gly Cys Arg
        115
```

(2) INFORMATION FOR SEQ ID NO:12:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Vgr-1

(ix) FEATURE:
        (A) NAME/KEY: Protein
        (B) LOCATION: 1..119

(xi) SEQUENCE DESCRIPTION: SEQ ID NO:12:

```
Ser Arg Gly Ser Gly Ser Ser Asp Tyr Asn Gly Ser Glu Leu Lys Thr
 1               5                  10                  15
```

Ala Cys Lys Lys His Glu Leu Tyr Val Ser Phe Gln Asp Leu Gly Trp
            20                  25                  30

Gln Asp Trp Ile Ile Ala Pro Lys Gly Tyr Ala Ala Asn Tyr Cys Asp
            35                  40                  45

Gly Glu Cys Ser Phe Pro Leu Asn Ala His Met Asn Ala Thr Asn His
50                  55                  60

Ala Ile Val Gln Thr Leu Val His Leu Met Asn Pro Glu Tyr Val Pro
65                  70                  75                  80

Lys Pro Cys Cys Ala Pro Thr Lys Leu Asn Ala Ile Ser Val Leu Tyr
            85                  90                  95

Phe Asp Asp Asn Ser Asn Val Ile Leu Lys Lys Tyr Arg Asn Met Val
            100                 105                 110

Val Arg Ala Cys Gly Cys His
            115

(2) INFORMATION FOR SEQ ID NO:13:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: OP-1

(ix) FEATURE:
        (A) NAME/KEY: Protein
        (B) LOCATION: 1..119

(xi) SEQUENCE DESCRIPTION: SEQ ID NO:13:

Leu Arg Met Ala Asn Val Ala Glu Asn Ser Ser Asp Gln Arg Gln
1               5                   10                  15

Ala Cys Lys Lys His Glu Leu Tyr Val Ser Phe Arg Asp Leu Gly Trp
            20                  25                  30

Gln Asp Trp Ile Ile Ala Pro Glu Gly Tyr Ala Ala Tyr Tyr Cys Glu
            35                  40                  45

Gly Glu Cys Ala Phe Pro Leu Asn Ser Tyr Met Asn Ala Thr Asn His
50                  55                  60

Ala Ile Val Gln Thr Leu Val His Phe Ile Asn Pro Glu Thr Val Pro
65                  70                  75                  80

Lys Pro Cys Cys Ala Pro Thr Gln Leu Asn Ala Ile Ser Val Leu Tyr
            85                  90                  95

Phe Asp Asp Ser Ser Asn Val Ile Leu Lys Lys Tyr Arg Asn Met Val
            100                 105                 110

Val Arg Ala Cys Gly Cys His
            115

(2) INFORMATION FOR SEQ ID NO:14:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: BMP-5

```
        (ix) FEATURE:
              (A) NAME/KEY: Protein
              (B) LOCATION: 1..119

(xi) SEQUENCE DESCRIPTION: SEQ ID NO:14:

Ser Arg Met Ser Ser Val Gly Asp Tyr Asn Thr Ser Glu Gln Lys Gln
1               5                   10                  15

Ala Cys Lys Lys His Glu Leu Tyr Val Ser Phe Arg Asp Leu Gly Trp
            20                  25                  30

Gln Asp Trp Ile Ile Ala Pro Glu Gly Tyr Ala Ala Phe Tyr Cys Asp
                35                  40                  45

Gly Glu Cys Ser Phe Pro Leu Asn Ala His Met Asn Ala Thr Asn His
    50                  55                  60

Ala Ile Val Gln Thr Leu Val His Leu Met Phe Pro Asp His Val Pro
65                  70                  75                  80

Lys Pro Cys Cys Ala Pro Thr Lys Leu Asn Ala Ile Ser Val Leu Tyr
                85                  90                  95

Phe Asp Asp Ser Ser Asn Val Ile Leu Lys Lys Tyr Arg Asn Met Val
                100                 105                 110

Val Arg Ser Cys Gly Cys His
            115

(2) INFORMATION FOR SEQ ID NO:15:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: OP-2

(ix) FEATURE:
        (A) NAME/KEY: Protein
        (B) LOCATION: 1..119

(xi) SEQUENCE DESCRIPTION: SEQ ID NO:15:

Arg Leu Pro Gly Ile Phe Asp Asp Val His Gly Ser His Gly Arg Gln
1               5                   10                  15

Val Cys Arg Arg His Glu Leu Tyr Val Ser Phe Gln Asp Leu Gly Trp
            20                  25                  30

Leu Asp Trp Val Ile Ala Pro Gln Gly Tyr Ser Ala Tyr Tyr Cys Glu
                35                  40                  45

Gly Glu Cys Ser Phe Pro Leu Asp Ser Cys Met Asn Ala Thr Asn His
    50                  55                  60

Ala Ile Leu Gln Ser Leu Val His Leu Met Lys Pro Asn Ala Val Pro
65                  70                  75                  80

Lys Ala Cys Cys Ala Pro Thr Lys Leu Ser Ala Thr Ser Val Leu Tyr
                85                  90                  95

Tyr Asp Ser Ser Asn Asn Val Ile Leu Arg Lys Ala Arg Asn Met Val
                100                 105                 110

Val Lys Ala Cys Gly Cys His
            115

(2) INFORMATION FOR SEQ ID NO:16:

(i) SEQUENCE CHARACTERISTICS:
        (A) LENGTH: 120 amino acids
```

```
          (B) TYPE: amino acid
          (C) STRANDEDNESS: single
          (D) TOPOLOGY: linear (ii) MOLECULE TYPE: protein (vii) IMMEDIATE SOURCE:
          (B) CLONE: BMP-3

(ix) FEATURE:
          (A) NAME/KEY: Protein
          (B) LOCATION: 1..120

(xi) SEQUENCE DESCRIPTION: SEQ ID NO:16:

Glu Gln Thr Leu Lys Lys Ala Arg Arg Lys Gln Trp Ile Glu Pro Arg
1               5                   10                  15

Asn Cys Ala Arg Arg Tyr Leu Lys Val Asp Phe Ala Asp Ile Gly Trp
            20                  25                  30

Ser Glu Trp Ile Ile Ser Pro Lys Ser Phe Asp Ala Tyr Tyr Cys Ser
        35                  40                  45

Gly Ala Cys Gln Phe Pro Met Pro Lys Ser Leu Lys Pro Ser Asn His
    50                  55                  60

Ala Thr Ile Gln Ser Ile Val Arg Ala Val Gly Val Val Pro Gly Ile
65                  70                  75                  80

Pro Glu Pro Cys Cys Val Pro Glu Lys Met Ser Ser Leu Ser Ile Leu
                85                  90                  95

Phe Phe Asp Glu Asn Lys Asn Val Val Leu Lys Val Tyr Pro Asn Met
            100                 105                 110

Thr Val Glu Ser Cys Ala Cys Arg
        115                 120

(2) INFORMATION FOR SEQ ID NO:17:

(i) SEQUENCE CHARACTERISTICS:
          (A) LENGTH: 116 amino acids
          (B) TYPE: amino acid
          (C) STRANDEDNESS: single
          (D) TOPOLOGY: linear (ii) MOLECULE TYPE: protein (vii) IMMEDIATE SOURCE:
          (B) CLONE: MIS (ix) FEATURE:
          (A) NAME/KEY: Protein
          (B) LOCATION: 1..116

(xi) SEQUENCE DESCRIPTION: SEQ ID NO:17:

Gly Pro Gly Arg Ala Gln Arg Ser Ala Gly Ala Thr Ala Ala Asp Gly
1               5                   10                  15

Pro Cys Ala Leu Arg Glu Leu Ser Val Asp Leu Arg Ala Glu Arg Ser
            20                  25                  30

Val Leu Ile Pro Glu Thr Tyr Gln Ala Asn Asn Cys Gln Gly Val Cys
        35                  40                  45

Gly Trp Pro Gln Ser Asp Arg Asn Pro Arg Tyr Gly Asn His Val Val
    50                  55                  60

Leu Leu Leu Lys Met Gln Ala Arg Gly Ala Ala Leu Ala Arg Pro Pro
65                  70                  75                  80

Cys Cys Val Pro Thr Ala Tyr Ala Gly Lys Leu Leu Ile Ser Leu Ser
                85                  90                  95

Glu Glu Arg Ile Ser Ala His His Val Pro Asn Met Val Ala Thr Glu
            100                 105                 110
```

```
Cys Gly Cys Arg
        115

(2) INFORMATION FOR SEQ ID NO:18:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Inhibin-alpha (ix) FEATURE:
        (A) NAME/KEY: Protein
        (B) LOCATION: 1..122

(xi) SEQUENCE DESCRIPTION: SEQ ID NO:18:

Ala Leu Arg Leu Leu Gln Arg Pro Pro Glu Glu Pro Ala Ala His Ala
1               5                   10                  15

Asn Cys His Arg Val Ala Leu Asn Ile Ser Phe Gln Glu Leu Gly Trp
            20                  25                  30

Glu Arg Trp Ile Val Tyr Pro Pro Ser Phe Ile Phe His Tyr Cys His
        35                  40                  45

Gly Gly Cys Gly Leu His Ile Pro Pro Asn Leu Ser Leu Pro Val Pro
50                  55                  60

Gly Ala Pro Pro Thr Pro Ala Gln Pro Tyr Ser Leu Leu Pro Gly Ala
65                  70                  75                  80

Gln Pro Cys Cys Ala Ala Leu Pro Gly Thr Met Arg Pro Leu His Val
                85                  90                  95

Arg Thr Thr Ser Asp Gly Gly Tyr Ser Phe Lys Tyr Glu Thr Val Pro
            100                 105                 110

Asn Leu Leu Thr Gln His Cys Ala Cys Ile
        115                 120

(2) INFORMATION FOR SEQ ID NO:19:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Inhibin-beta-A (ix) FEATURE:
        (A) NAME/KEY: Protein
        (B) LOCATION: 1..121

(xi) SEQUENCE DESCRIPTION: SEQ ID NO:19:

Arg Arg Arg Arg Arg Gly Leu Glu Cys Asp Gly Lys Val Asn Ile Cys
1               5                   10                  15

Cys Lys Lys Gln Phe Phe Val Ser Phe Lys Asp Ile Gly Trp Asn Asp
            20                  25                  30

Trp Ile Ile Ala Pro Ser Gly Tyr His Ala Asn Tyr Cys Glu Gly Glu
        35                  40                  45

Cys Pro Ser His Ile Ala Gly Thr Ser Gly Ser Ser Leu Ser Phe His
50                  55                  60
```

```
Ser Thr Val Ile Asn His Tyr Arg Met Arg Gly His Ser Pro Phe Ala
 65                  70                  75                  80

Asn Leu Lys Ser Cys Cys Val Pro Thr Lys Leu Arg Pro Met Ser Met
                 85                  90                  95

Leu Tyr Tyr Asp Asp Gly Gln Asn Ile Ile Lys Lys Asp Ile Gln Asn
                100                 105                 110

Met Ile Val Glu Glu Cys Gly Cys Ser
            115                 120
```

(2) INFORMATION FOR SEQ ID NO:20:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Inhibin-beta-B (ix) FEATURE:
        (A) NAME/KEY: Protein
        (B) LOCATION: 1..120

(xi) SEQUENCE DESCRIPTION: SEQ ID NO:20:

```
Arg Ile Arg Lys Arg Gly Leu Glu Cys Asp Gly Arg Thr Asn Leu Cys
 1               5                  10                  15

Cys Arg Gln Gln Phe Phe Ile Asp Phe Arg Leu Ile Gly Trp Asn Asp
                 20                  25                  30

Trp Ile Ile Ala Pro Thr Gly Tyr Tyr Gly Asn Tyr Cys Glu Gly Ser
             35                  40                  45

Cys Pro Ala Tyr Leu Ala Gly Val Pro Gly Ser Ala Ser Ser Phe His
         50                  55                  60

Thr Ala Val Val Asn Gln Tyr Arg Met Arg Gly Leu Asn Pro Gly Thr
 65                  70                  75                  80

Val Asn Ser Cys Cys Ile Pro Thr Lys Leu Ser Thr Met Ser Met Leu
                 85                  90                  95

Tyr Phe Asp Asp Glu Tyr Asn Ile Val Lys Arg Asp Val Pro Asn Met
                100                 105                 110

Ile Val Glu Glu Cys Gly Cys Ala
            115                 120
```

(2) INFORMATION FOR SEQ ID NO:21:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Nodal (ix) FEATURE:
        (A) NAME/KEY: Protein
        (B) LOCATION: 1..118

(xi) SEQUENCE DESCRIPTION: SEQ ID NO:21:

```
Gly Trp Gly Arg Arg Gln Arg Arg His His Leu Pro Asp Arg Ser Gln
 1               5                  10                  15
```

Leu Cys Arg Arg Val Lys Phe Gln Val Asp Phe Asn Leu Ile Gly Trp
            20                  25                  30

Gly Ser Trp Ile Ile Tyr Pro Lys Gln Tyr Asn Ala Tyr Arg Cys Glu
        35                  40                  45

Gly Glu Cys Pro Asn Pro Val Gly Glu Glu Phe His Pro Thr Asn His
50                  55                  60

Ala Tyr Ile Gln Ser Leu Leu Lys Arg Tyr Gln Pro His Arg Val Pro
65                  70                  75                  80

Ser Thr Cys Cys Ala Pro Val Lys Thr Lys Pro Leu Ser Met Leu Tyr
            85                  90                  95

Val Asp Asn Gly Arg Val Leu Leu Glu His His Lys Asp Met Ile Val
            100                 105                 110

Glu Glu Cys Gly Cys Leu
        115

(2) INFORMATION FOR SEQ ID NO:22:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta-1

(ix) FEATURE:
        (A) NAME/KEY: Protein
        (B) LOCATION: 1..114

(xi) SEQUENCE DESCRIPTION: SEQ ID NO:22:

Arg Arg Ala Leu Asp Thr Asn Tyr Cys Phe Ser Ser Thr Glu Lys Asn
1               5                   10                  15

Cys Cys Val Arg Gln Leu Tyr Ile Asp Phe Arg Lys Asp Leu Gly Trp
            20                  25                  30

Lys Trp Ile His Glu Pro Lys Gly Tyr His Ala Asn Phe Cys Leu Gly
        35                  40                  45

Pro Cys Pro Tyr Ile Trp Ser Leu Asp Thr Gln Tyr Ser Lys Val Leu
    50                  55                  60

Ala Leu Tyr Asn Gln His Asn Pro Gly Ala Ser Ala Ala Pro Cys Cys
65                  70                  75                  80

Val Pro Gln Ala Leu Glu Pro Leu Pro Ile Val Tyr Tyr Val Gly Arg
            85                  90                  95

Lys Pro Lys Val Glu Gln Leu Ser Asn Met Ile Val Arg Ser Cys Lys
            100                 105                 110

Cys Ser (2) INFORMATION FOR SEQ ID NO:23:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TGF-beta-2

(ix) FEATURE:
            (A) NAME/KEY: Protein
            (B) LOCATION: 1..114

(xi) SEQUENCE DESCRIPTION: SEQ ID NO:23:

Lys Arg Ala Leu Asp Ala Ala Tyr Cys Phe Arg Asn Val Gln Asp Asn
1               5                   10                  15

Cys Cys Leu Arg Pro Leu Tyr Ile Asp Phe Lys Arg Asp Leu Gly Trp
                20                  25                  30

Lys Trp Ile His Glu Pro Lys Gly Tyr Asn Ala Asn Phe Cys Ala Gly
            35                  40                  45

Ala Cys Pro Tyr Leu Trp Ser Ser Asp Thr Gln His Ser Arg Val Leu
    50                  55                  60

Ser Leu Tyr Asn Thr Ile Asn Pro Glu Ala Ser Ala Ser Pro Cys Cys
65                  70                  75                  80

Val Ser Gln Asp Leu Glu Pro Leu Thr Ile Leu Tyr Tyr Ile Gly Lys
                85                  90                  95

Thr Pro Lys Ile Glu Gln Leu Ser Asn Met Ile Val Lys Ser Cys Lys
            100                 105                 110

Cys Ser (2) INFORMATION FOR SEQ ID NO:24:

(i) SEQUENCE CHARACTERISTICS:
            (A) LENGTH: 114 amino acids
            (B) TYPE: amino acid
            (C) STRANDEDNESS: single
            (D) TOPOLOGY: linear (ii) MOLECULE TYPE: protein (vii) IMMEDIATE SOURCE:
            (B) CLONE: TGF-beta-3

(ix) FEATURE:
            (A) NAME/KEY: Protein
            (B) LOCATION: 1..114

(xi) SEQUENCE DESCRIPTION: SEQ ID NO:24:

Lys Arg Ala Leu Asp Thr Asn Tyr Cys Phe Arg Asn Leu Glu Glu Asn
1               5                   10                  15

Cys Cys Val Arg Pro Leu Tyr Ile Asp Phe Arg Gln Asp Leu Gly Trp
                20                  25                  30

Lys Trp Val His Glu Pro Lys Gly Tyr Tyr Ala Asn Phe Cys Ser Gly
            35                  40                  45

Pro Cys Pro Tyr Leu Arg Ser Ala Asp Thr Thr His Ser Thr Val Leu
    50                  55                  60

Gly Leu Tyr Asn Thr Leu Asn Pro Glu Ala Ser Ala Ser Pro Cys Cys
65                  70                  75                  80

Val Pro Gln Asp Leu Glu Pro Leu Thr Ile Leu Tyr Tyr Val Gly Arg
                85                  90                  95

Thr Pro Lys Val Glu Gln Leu Ser Asn Met Val Val Lys Ser Cys Lys
            100                 105                 110

Cys Ser (2) INFORMATION FOR SEQ ID NO:25:

(i) SEQUENCE CHARACTERISTICS:
            (A) LENGTH: 115 amino acids
            (B) TYPE: amino acid
            (C) STRANDEDNESS: single

```
        (D) TOPOLOGY: linear (ii) MOLECULE TYPE: protein (vii) IMMEDIATE SOURCE:
         (B) CLONE: Human GDF-10

(ix) FEATURE:
         (A) NAME/KEY: Protein
         (B) LOCATION: 1..115

(xi) SEQUENCE DESCRIPTION: SEQ ID NO:25:

Lys Ala Arg Arg Lys Gln Trp Asp Glu Pro Arg Val Cys Ser Arg Arg
1               5                   10                  15

Tyr Leu Lys Val Asp Phe Ala Asp Ile Gly Trp Asn Glu Trp Ile Ile
            20                  25                  30

Ser Pro Lys Ser Phe Asp Ala Tyr Tyr Cys Ala Gly Ala Cys Glu Phe
        35                  40                  45

Pro Met Pro Lys Ile Val Arg Pro Ser Asn His Ala Thr Ile Gln Ser
    50                  55                  60

Ile Val Arg Ala Val Gly Ile Ile Pro Gly Ile Pro Glu Pro Cys Cys
65                  70                  75                  80

Val Pro Asp Lys Met Asn Ser Leu Gly Val Leu Phe Leu Asp Glu Asn
                85                  90                  95

Arg Asn Val Val Leu Lys Val Tyr Pro Asn Met Ser Val Asp Thr Cys
            100                 105                 110

Ala Cys Arg
        115

(2) INFORMATION FOR SEQ ID NO:26:

(i) SEQUENCE CHARACTERISTICS:
         (A) LENGTH: 115 amino acids
         (B) TYPE: amino acid
         (C) STRANDEDNESS: single
         (D) TOPOLOGY: linear (ii) MOLECULE TYPE: protein (vii) IMMEDIATE SOURCE:
         (B) CLONE: Murine GDF-10

(ix) FEATURE:
         (A) NAME/KEY: Protein
         (B) LOCATION: 1..115

(xi) SEQUENCE DESCRIPTION: SEQ ID NO:26:

Lys Ala Arg Arg Lys Gln Trp Asp Glu Pro Arg Val Cys Ser Arg Arg
1               5                   10                  15

Tyr Leu Lys Val Asp Phe Ala Asp Ile Gly Trp Asn Glu Trp Ile Ile
            20                  25                  30

Ser Pro Lys Ser Phe Asp Ala Tyr Tyr Cys Ala Gly Ala Cys Glu Phe
        35                  40                  45

Pro Met Pro Lys Ile Val Arg Pro Ser Asn His Ala Thr Ile Gln Ser
    50                  55                  60

Ile Val Arg Ala Val Gly Ile Val Pro Gly Ile Pro Glu Pro Cys Cys
65                  70                  75                  80

Val Pro Asp Lys Met Asn Ser Leu Gly Val Leu Phe Leu Asp Glu Asn
                85                  90                  95
```

-continued

```
Arg Asn Ala Val Leu Lys Val Tyr Pro Asn Met Ser Val Glu Thr Cys
            100                 105                 110
Ala Cys Arg
        115
```